United States Patent [19]
Eysel et al.

[11] Patent Number: 5,473,160
[45] Date of Patent: Dec. 5, 1995

[54] METHOD FOR DIAGNOSING ARTHRITIC DISORDERS BY INFRARED SPECTROSCOPY

[75] Inventors: Hans H. Eysel; Michael Jackson; Henry H. Mantsch, all of Manitoba, Canada

[73] Assignee: National Research Council of Canada, Ottawa, Canada

[21] Appl. No.: 288,321

[22] Filed: Aug. 10, 1994

[51] Int. Cl.$^6$ .................................................. G01N 21/35
[52] U.S. Cl. ...................................... 250/339.12; 250/343
[58] Field of Search ........................... 250/339.12, 341.8, 250/343, 339.11

[56] References Cited

U.S. PATENT DOCUMENTS

| | | | |
|---|---|---|---|
| 4,988,211 | 1/1991 | Barnes et al. | 374/121 |
| 5,038,039 | 8/1991 | Wong et al. | 250/339.12 |
| 5,168,162 | 12/1992 | Wong et al. | 250/339.12 |

OTHER PUBLICATIONS

Eysel et al., "Carbon Dioxide Clathrates: An IR Spectroscopic Marker for Arthritis?", Applied Spectroscopy, vol. 47, No. 9, 1993, pp. 1519–1521.

*Primary Examiner*—Carolyn E. Fields
*Assistant Examiner*—Edward J. Glick
*Attorney, Agent, or Firm*—Juliusz Szereszewski

[57] ABSTRACT

Differences in the physical and chemical properties of synovial fluid from healthy and arthritic joints are detected by infrared spectroscopy. A beam of infrared light is directed at a sample of synovial fluid (either in its native form or prepared as a film) and changes in the physical and chemical properties of the fluid being analyzed are detected at one or more wavelengths to determine whether changes in the position, width, absolute intensity, relative intensity or shape of the infrared absorption have occurred which are characteristic of the arthritic condition.

15 Claims, 4 Drawing Sheets

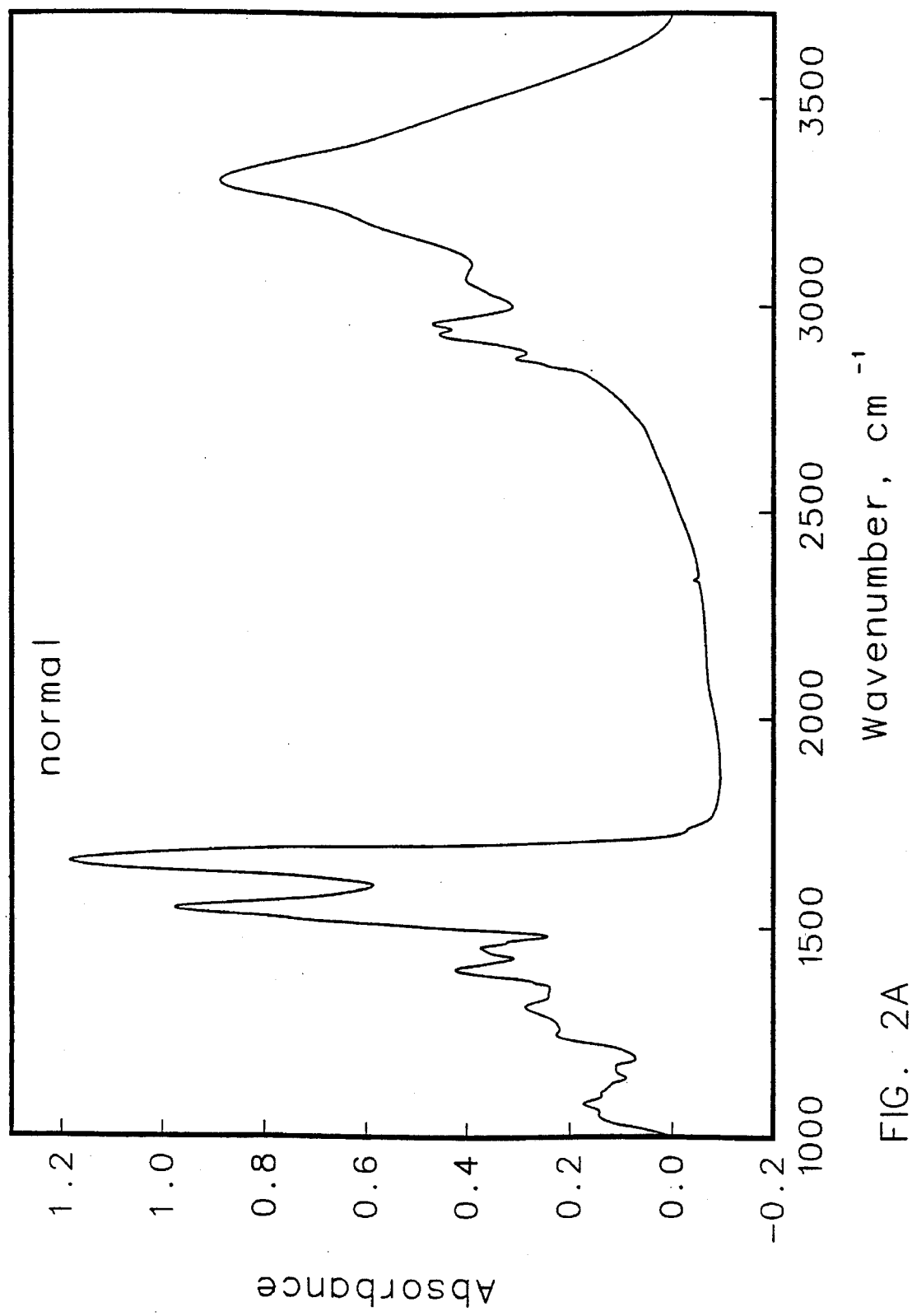

METHOD FOR DIAGNOSING ARTHRITIC DISORDERS BY INFRARED SPECTROSCOPY

FIELD OF THE INVENTION

This invention relates to a method for diagnosing arthritic disorders based upon an infrared spectroscopic analysis of synovial fluids.

BACKGROUND OF THE INVENTION

Currently, diagnosis of arthritic disorders requires physical examination of the patient by a skilled medical practitioner, immunological examination of synovial fluid and/or blood, X-ray investigation, magnetic resonance imaging (MRI) or any combination of the these procedures. Such procedures:

i) require the services of a rheumatology specialist, immunologists and skilled technical staff,
ii) are time consuming and costly,
iii) are not always reliable
iv) can only detect arthritic disorders after severe damage to the affected joint has already appeared.

There is therefore the need for a rapid, non-subjective, low cost and non-labour intensive method for the diagnosis of arthritic disorders which does not require highly skilled personnel.

It has been proposed in U.S. Pat. No. 5,038,039 dated Aug. 6th 1991, "Method of Detecting the Presence of Anomalies in Biological Tissues and Cells in Natural and Cultured Form by Infrared Spectroscopy", P. T. T. Wong and B. Rigas, that infrared spectroscopy can be used to detect anomalies in biological tissues and cells. Such a method is not easily applicable to the diagnosis of arthritic disorders, as tissue from the affected joints is not usually available. This method does not include infrared spectroscopic analysis of biological fluids, due to the inherent problems associated with such an analysis caused by the presence of extremely strong interfering infrared absorptions from the water present in biological fluids.

It has been reported that the intensity of a novel infrared absorption band observed in synovial fluid films may be useful as an indicator of arthritis (Eysel et al., Applied Spectroscopy Vol. 47, No. 9, p. 1519–1521, 1993). However, this feature, attributed to metabolically produced $CO_2$ trapped within the matrix of the film, may be considered to be a marker of inflammatory conditions, which are accompanied by increased metabolic activity and so elevated levels of $CO_2$. Thus such a technique would provide a metabolic profile of the joint (which may, for example be affected by infection) rather than a clinically relevant diagnosis of arthritis. The invention reported here on the other hand concentrates on differences in the physical and chemical properties of synovial fluid which directly result from or cause degeneration of the joint and which are represented as changes in the infrared spectrum of the fluid or film.

Russian Patent No. 1,686,357 issued Oct. 23, 1991 discloses a method for diagnosing rheumatoid arthritis activity level by isolating erythrocyte suspension from blood, recording an EPR spectrum and determining the arthritic activity.

U.S. Pat. No. 4,499,186 issued Feb. 12, 1985 to Teodorescu et al. describes a spectrophotometric diagnosis of rheumatoid arthritis by blocking calcium ions in a blood sample.

SUMMARY OF THE INVENTION

According to the present invention, there is described an infrared spectroscopic method for the detection of anomalies in joint physiology, based upon infrared spectroscopic analysis of the synovial fluid from affected joints, which can provide rapid and accurate diagnosis of arthritic disorders without the problems normally associated with the presence of water in the fluid. The method comprises the steps of directing a beam of infrared light at a sample of the synovial fluid from the joint, or a film formed from the fluid, and determining by spectroscopic analysis and optionally statistical analysis whether variation in the infrared absorption of any functional group, characteristic of the anomaly, has occurred.

The anomaly may be osteoarthritis, rheumatoid arthritis, ankylosing spondylitis, reactive arthritis, spondyloarthropathy, Crohn's disease, lupus, Still's disease, gout, or pseudogout.

The method may be directed at monitoring changes in the anomaly due to therapeutic intervention.

BRIEF DESCRIPTION OF THE DRAWINGS

In the drawings

FIG. 2A illustrates representative IR spectra of normal synovial fluid films.

DETAILED DESCRIPTION OF THE INVENTION

Figure 1:
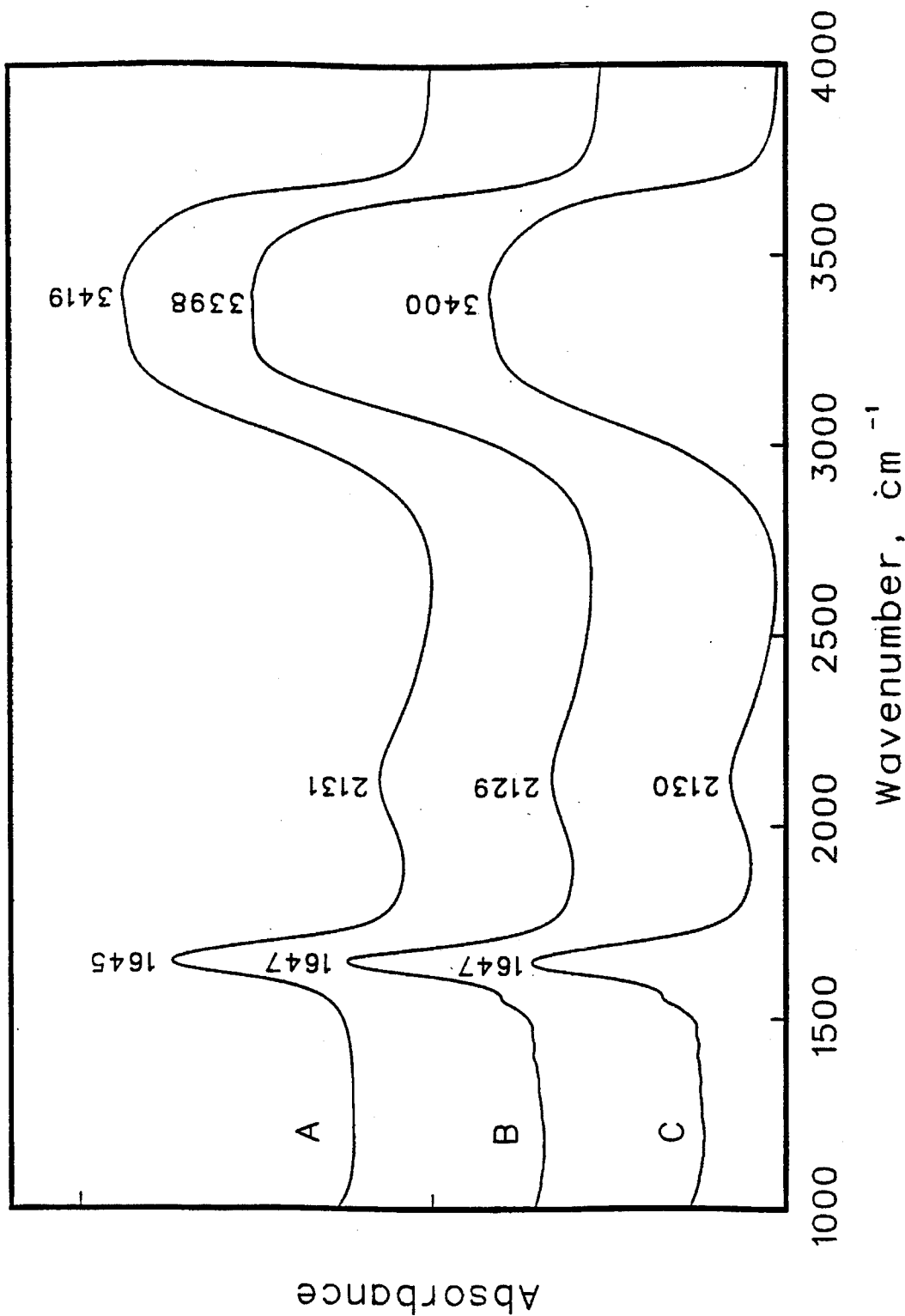
FIG. 1 illustrates infrared spectra of water (A), control (B) and osteoarthritic synovial fluid (C)

In this specification, the expression "synovial fluid" refers to the fluid obtained from joints by needle aspiration or other means (including surgery) and includes freshly aspirated fluids, fluids stored in heparinised and non-heparinised containers, fluids containing anticoagulants and fluids which have been stored at subambient temperature. The expression synovial fluid film refers to films formed by the evaporation of water from any of the above mentioned synovial fluids either at ambient temperature and pressure or with manipulations of the temperature and pressure.

The sample to be analyzed may be placed between windows composed of any infrared transparent material, deposited on any reflective surface or upon any surface which does not interact with the sample in an irreproducible manner.

The sample may be analyzed to generate a transmission/absorbance, transflection (back-scattering), reflectance, attenuated total reflectance or photoacoustic spectrum.

The spectroscopic analysis may be carried out with the sample subjected to elevated pressure to render detectable the infrared absorption or change in the absorption(s) characteristics of the anomaly.

The spectroscopic analysis may be carried out using a Fourier transform infrared spectrometer, a grating or prism infrared spectrometer, an acousto-optical tunable filter infrared spectrometer, a filter infrared spectrometer or an infrared spectrometer using a tunable infrared source.

The spectroscopic analysis may be carried out in one or both of those regions of the electromagnetic spectrum termed the mid and near infrared regions.

In transmission/absorbance operation for synovial fluid analysis, a small volume of synovial fluid is placed between a pair of infrared transparent windows and a beam of infrared light passed through the sample onto a detector. Any infrared anomaly in the sample is detected by the infrared spectrometer. The resolution of the spectrum is not critical; resolutions in the range 2–16 $cm^{-6}$ have proven to be diagnostically useful.

In transmission/absorbance operation for synovial fluid film analysis, the film is prepared by drying at ambient temperature and pressure, at reduced pressure and ambient temperature or at reduced pressure and elevated temperature upon a suitable substrate. Drying at reduced pressure and elevated temperatures reduces preparation time and produces even films but is not essential.

In reflectance and transflection operation for synovial fluid film analysis, the film is deposited as described above on any reflective surface, for example polished metal or metal coated substrates.

In attenuated total reflectance operation for synovial fluid and synovial fluid film analysis any attenuated total internal reflectance element having the required refractive index and transmittance characteristics may be used.

Tests have shown that for a variety of arthritic conditions, spectral changes in the mid and near infrared regions of the spectrum can be used for diagnostic purposes. The following examples are typical of the tests that were carried out in the mid infrared region of the spectrum and indicate how diagnosis may be achieved by examination of spectral changes and statistical analysis of these changes.

Samples of synovial fluid were obtained by needle aspiration of the knee or ankle joints of patients suffering from a variety of arthritic disorders. Control synovial fluid was obtained from the knee joints of patients during surgery for traumatic knee injury. Samples were stored in non-heparinised containers (subsequent investigations have demonstrated that heparinised containers do not pose a problem) before use. A portion of the sample was retained by the clinician for clinical diagnosis. Samples were analyzed as soon as possible after acquisition, although low temperature storage of the samples did not impair diagnosis.

For spectroscopic analysis of films, small volumes (typically 20 μl.) of sample were pipetted onto an infrared transparent substrate (typically $CaF_2$) and dried under a light vacuum at 37° C. to speed drying. For spectroscopic analysis of fluids, a small volume of fluid was placed between a pair of infrared transparent windows separated by a 6 μm spacer. Alternatively, a cell incorporating a machined window containing a 6 μm depression may be used to avoid the use of a spacer and to obtain a more reproducible pathlength.

Spectra were measured on a Digilab FTS 40A Fourier transform infrared spectrometer equipped with a liquid nitrogen cooled mercury-cadmium-telluride detector. For each sample, 256 scans were coadded at a nominal resolution of 2 $cm^{-1}$ in the range 800–4000 $cm^{-1}$.

Typical spectra are shown in FIG. 1, wherein the spectrum designated A denotes water and the spectrum designated B denotes the results on control synovial fluid. The trace designated C in FIG. 1 is the spectrum of synovial fluid from a rheumatoid arthritic knee. Spectra in the region shown in FIG. 1 are dominated by absorptions from water.

While the presence of dominant absorptions attributed to the water is generally considered a drawback by practitioners of the art, in the present invention it has significant diagnostic value. It is apparent from FIG. 1 that significant differences exist both in the shape and position of the major water absorptions in the three spectra. These differences must arise from alterations in the structure of the water, that is, in differences in the intermolecular hydrogen bonding pattern that characterises water. These differences are in turn related to the presence of large concentrations of macromolecules in the synovial fluid, which have significant interactions with water molecules, so disrupting water-water hydrogen bonds. As the composition of the fluid changes in disease states, so the nature of the differences between the synovial fluid water and bulk water will vary. This is illustrated with an examination of the frequency of the combination band of water, which in pure water is seen at 2131 $cm^{-1}$ and in control synovial fluid is seen at 2129 $cm^{-1}$. In rheumatoid arthritis the frequency of this band is intermediate between that seen in water and control synovial fluid, indicating that the structure of the water is intermediate between that seen in pure water and control synovial fluid. The variation in the frequency and shape of the band is therefore of diagnostic use.

Figure 2B:
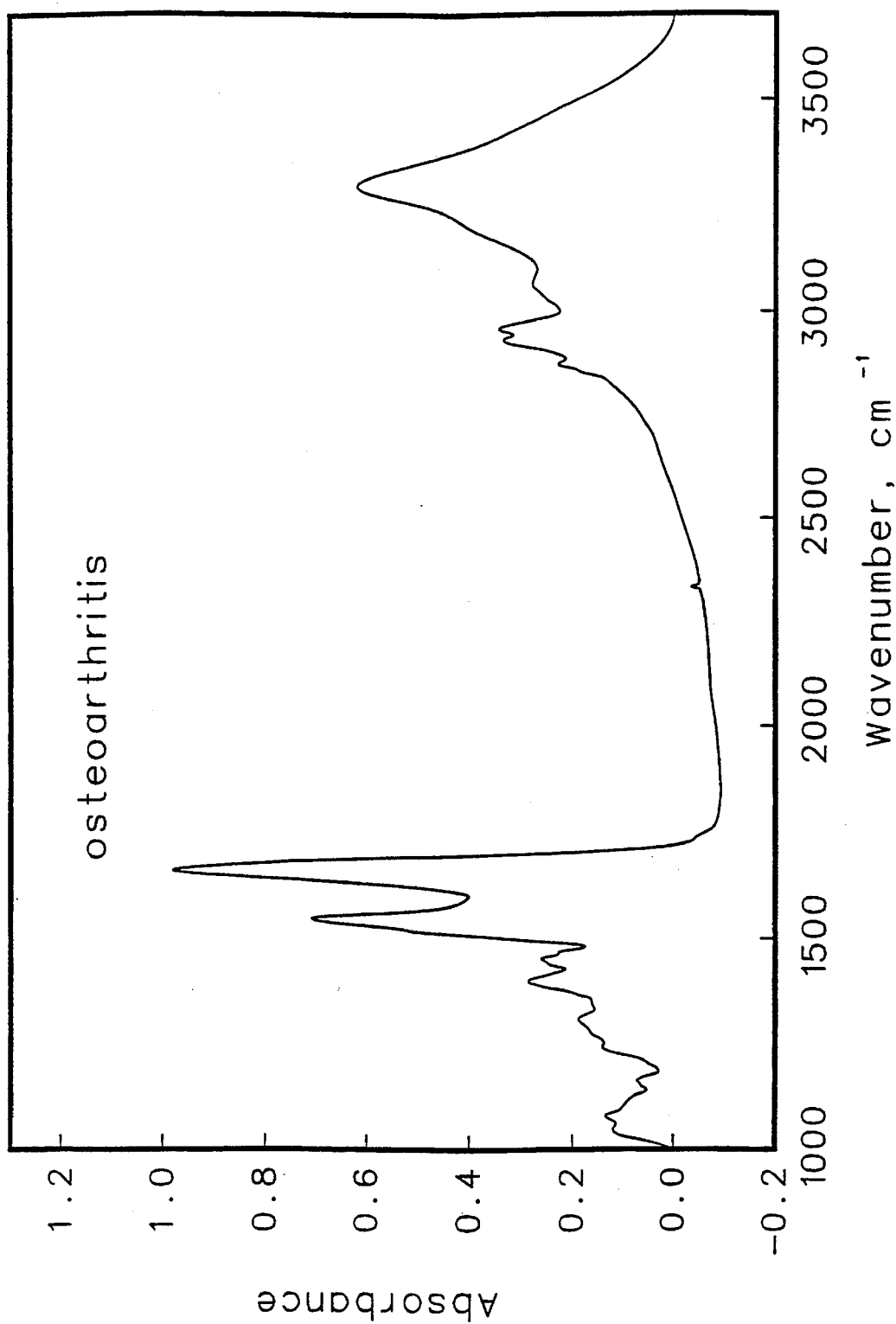
FIG. 2B illustrates representative spectra of osteoarthritic synovial fluid films.
Figure 2C:
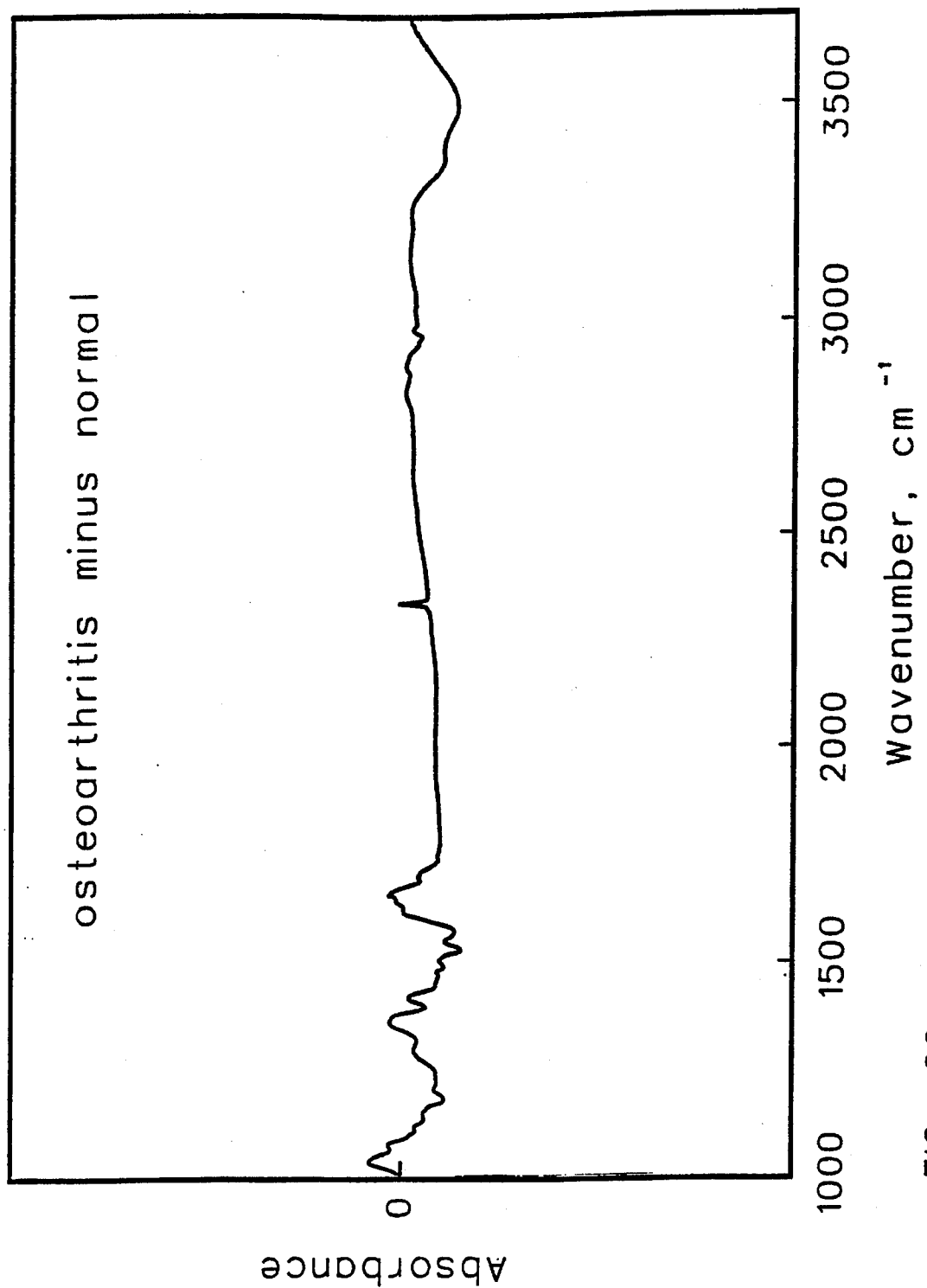
FIG. 2C illustrates the difference spectrum generated by subtraction of spectrum of FIG. 2A from spectrum of FIG. 2B.

The variation in the structure of the solvent water present in synovial fluid varies, as discussed, which makes it impossible to subtract a reference spectrum of water from the fluid to obtain a spectrum of the macromolecules present in the fluid. This problem may be resolved by removal of the water from the fluid by drying. Representative spectra of a synovial fluid film formed from the fluid obtained from a non-arthritic knee and the knee of a patient suffering from osteoarthritis are shown in FIGS. 2A and 2B, respectively. Shown in FIG. 2C is a difference spectrum generated by the digital subtraction of the class average spectrum of normal synovial fluid films from the class average of osteoarthritic fluid films. It is apparent that subtle but important differences exist between spectra of normal and diseased synovial fluid films. Similar differences are found between the class average spectra of films formed from synovial fluids obtained from joints affected by rheumatoid arthritis and spondyloarthropathy and normal joints. Such differences may be related to variations in the concentration of macromolecules within the joint caused by alterations in joint physiology. For example, the spectral range 1000–1200 $cm^{-1}$ in spectra of synovial fluid films is dominated by absorptions arising from C—O stretching vibrations of hyaluronic acid, and differences in this spectral region may be attributed to degradation of hyaluronic acid during the disease process. Degradation of hyaluronic acid leads to a reduced viscosity of synovial fluid, which markedly reduces its lubricating properties and leads to increased friction within the joint.

It will be appreciated that interpretation of IR spectra of synovial fluid and its films may still contain an element of subjectivity. This may be removed by performing multivariate statistical analyses upon infrared spectra of synovial fluids and films formed from synovial fluids to allow non-subjective diagnosis of joint abnormalities.

We claim:

1. A method for detecting the presence of anomalies in joints by infrared spectroscopy, comprising:

a) directing a beam of infrared light at a sample of a fluid taken from a joint or a film formed from said fluid to obtain an infrared spectrum of the sample, and b) determining by spectroscopic analysis of the infrared spectrum whether variation in the infrared absorption of any functional group present in the sample has occurred which is characteristic of an anomaly in the joint.

2. The method according to claim 1 wherein the anomaly is osteoarthritis.

3. The method according to claim 1 wherein the anomaly is rheumatoid arthritis.

4. The method according to claim 1 wherein the anomaly is ankylosing spondylitis.

5. The method according to claim 1 wherein the anomaly is reactive arthritis.

6. The method according to claim 1 wherein the anomaly is spondyloarthropathy.

7. The method according to claim 1 wherein the anomaly is Crohn's disease.

8. The method according to claim 1 wherein the anomaly is lupus.

9. The method according to claim 1 wherein the anomaly is Still's disease.

10. The method according to claim 1 wherein the anomaly is gout.

11. The method according to claim 1 wherein the anomaly is pseudogout.

12. The method according to claim 1 wherein changes in the anomaly due to therapeutic intervention are monitored.

13. The method according to claim 1 wherein the spectrum is at least one of mid and near infrared region of the spectrum.

14. The method according to claim 1 wherein the spectroscopic analysis is carried out on a spectrum selected from the group consisting of transmission/absorbance, transflection, reflectance, attenuated total reflectance, or photoacoustic spectrum.

15. The method of claim 1 further comprising multivariate statistical analysis to determine whether variation in the infrared absorption has occurred.

* * * * *